US00RE33850E

United States Patent [19]

Snyder et al.

[11] E Patent Number: Re. 33,850

[45] Reissued Date of Patent: Mar. 17, 1992

[54] TEST KIT AND METHOD FOR THE DETERMINATION OF STREPTOCOCCUS A ANTIGEN

[75] Inventors: Brian A. Snyder; Paul B. Contestable, both of Rochester, N.Y.

[73] Assignee: Eastman Kodak Company, Rochester, N.Y.

[21] Appl. No.: 509,648

[22] Filed: Feb. 20, 1990

Related U.S. Patent Documents

Reissue of:

[64] Patent No.: 4,808,524
Issued: Feb. 28, 1989
Appl. No.: 131,618
Filed: Dec. 11, 1987

U.S. Applications:

[63] Continuation-in-part of Ser. No. 98,431, Sep. 18, 1987, abandoned.

[51] Int. Cl.[5] ..... G01N 33/546; G01N 33/547; G01N 33/569

[52] U.S. Cl. ..... 435/7.34; 422/57; 422/61; 435/34; 435/36; 435/810; 435/961; 435/975; 436/519; 436/533; 436/534

[58] Field of Search ..... 435/34, 36, 810, 7.34, 435/961, 975; 436/519, 533, 534; 422/57, 61

[56] References Cited

U.S. PATENT DOCUMENTS 4,618,576 10/1986 Rosenstein et al. ..... 435/7
4,639,419 1/1987 Olson et al. ..... 436/810 X
4,673,639 6/1987 Slifkin ..... 435/36
4,851,337 7/1989 Berke ..... 435/29

FOREIGN PATENT DOCUMENTS 150567 8/1985 European Pat. Off. .

OTHER PUBLICATIONS

Slifkin et al., *J. Clin. Microbiol.* 15 (1) 1982, pp. 187–189.
Slifkin et al., *J. Clin. Microbiol.* 20 (1) 1984, pp. 12–14.
Guinet et al., *Med. Microbiol. Immunol.* 171 1982, pp. 23–32.

*Primary Examiner*—David A. Saunders
*Attorney, Agent, or Firm*—J. Lanny Tucker

[57] ABSTRACT

A test kit useful for the determination of Streptococcus A antigen comprises: (i) an immunoreactive reagent comprising either Streptococcus A antigen or antibodies attached to water-insoluble particles, (ii) a substrate having thereon a dried, binder-free coating of a first extraction reagent, (iii) an aqueous solution of a second extraction reagent, and (iv) a neutralizing solution. Both extraction reagents combine to provide nitrous acid. In addition, an extraction device includes a water-insoluble container having affixed therein the first extraction reagent and an applicator means for collecting and depositing a biological specimen within the container. The extraction device and test kit are useful to the determination of Streptococcus A antigen in a biological specimen.

14 Claims, No Drawings

TEST KIT AND METHOD FOR THE DETERMINATION OF STREPTOCOCCUS A ANTIGEN

Matter enclosed in heavy brackets [ ] appears in the original patent but forms no part of this reissue specification; matter printed in italics indicates the additions made by reissue.

RELATED APPLICATION

[This application] *This is a reissue of U.S. Pat. No. 4,808,524 (issued Feb. 28, 1989) based on U.S. Ser. No. 131,618 (filed Dec. 11, 1987) which* is a continuation-in-part application of U.S. Ser. No. 98,431 filed Sept. 18, 1987, now abandoned.

FIELD OF THE INVENTION

This invention relates to a test kit for the determination of Streptococcus A antigen, an extraction device for extracting antigen from the Streptococcus organisms and to a method of determining the antigen.

BACKGROUND OF THE INVENTION

The antigen-antibody reaction is the basis for all immunological test methods. Certain proteins known as antibodies are produced by mammals in response to the presence of an antigen, that is a foreign substance, which can be another protein or a carbohydrate. This normal body response to a foreign substance has led to the development of a number of techniques which are used to diagnose various diseases, disorders and physiological conditions. In a general sense, the component of the antibody-antigen reaction to be detected is defined herein as the immune species while the other corresponding component is considered the receptor.

For example, in vitro tests for the presence of a suspected protein, antigen or antibody in a biological sample are carried out by adding the immunological counterpart to the biological sample. If the suspected substance is present, the resulting antigen-antibody reaction can be demonstrated by precipitation of the antigen-antibody complex. This reaction complex is generally difficult to detect visually. For this reason, either antibodies or antigens are often bound to insoluble particles, for example polymer latex particles, so that when the complex is formed, it is readily detectable from the resulting agglutination either by observing the presence of clumping or a detectable tracer associated with the particles. Agglutination then is characterized by the clumping of particles from a suspension of particles. Further details of known agglutination methods are provided in U.S. Pat. Nos. 4,419,453 (issued Dec. 6, 1983 to Dorman et al.) and 4,459,361 (issued July 10, 1984 to Gefter).

Of the several groups of Streptococci, group A Streptococcus (S. pyogenes) is primarily responsible for causing pathological conditions in humans, such as B-hemolytic pneumonia, scarlet fever, rheumatic fever, cardiac sequelae, glomerulonephritis, septic sore throat and puerperal sepsis. Because of the serious nature of infections potentially caused by Streptococcus A, it is important to diagnose its presence in an early stage of infection so that an appropriate course of treatment may be selected. Early tests for detection required culturing a biological sample for long periods of time, usually at least 18 and up to 48 hours. In most cases, such lengthy tests delay treatment making them undesirable. Some doctors must forward test cultures to laboratories for evaluation by mail or courier, thereby delaying treatment further.

Most recent tests for Streptococcus A have been described which are allegedly quicker than the culturing techniques. U.S. Pat. No. 4,618,576 (issued Oct. 21, 1986 to Rosenstein et al.) describes an agglutination test using certain enzymes to extract the antigen directly from the swab used to obtain a specimen from the throat. A kit comprising an applicator means for collecting the specimen, an extraction reagent containing the enzymes and suitable indicator reagents is also described. The described method is disadvantageous because the agglutinate is not readily observable except with a microscope, and requires extraction enzymes prepared from a bacterium which must be cultured.

Another agglutination assay is described in E. P. Publication No. 150,567 (Meridian Diagnostics, published Aug. 7, 1985). This assay describes an extraction technique which uses a solution of sodium nitrite combined with glacial acetic acid. This assay has a serious disadvantage, however, because the extraction composition is not easily stored, transported or handled. Acetic acid is a volatile liquid at room temperature, the normal conditions of use. It therefore presents problems in long-term storage and ease of handling.

U.S. Pat. No. 4,673,639 (issued June 16, 1987 to Slifkin) allegedly describes a means for overcoming the problems associated with volatile extraction reagents. This reference proposes affixing one or both extraction reagents, in combination with a water-soluble binder material, in a ready-to-use microtube. The reagents used include a nonvolatile acid, such as citric acid. The patent also teaches a further advantage of this method over known assays in that a neutralizing step is unnecessary (see Col. 4, line 4–18). Eliminating this step allegedly has no adverse effects on the agglutination reagents used or the assay results.

We have found that elimination of a neutralizing step adversely affects certain agglutination reagents in an assay for Streptococcus A antigen. It can also adversely affect antibodies if they are in a low pH environment too long. Furthermore, it would be desirable to eliminate the need for using a binder material to immobilize extraction reagents because of the additional material and manufacturing expense they engender.

SUMMARY OF THE INVENTION

The problems noted above with known test kits and Streptococcus A assays are overcome with a test kit for the determination of Streptococcus A antigen comprising:

(a) a water-insoluble substrate having thereon a dried, binder-free coating of a first extraction reagent which is necessary for nitrous acid extraction of the antigen from a Streptococcus A organism, (b) an aqueous solution of a second extraction reagent which is necessary for the nitrous acid extraction, (c) a neutralizing solution having a pH of from about 5 to about 10, and (d) a sample of an immunoreactive reagent comprising water-insoluble particles having either Streptococcus A antigen or antibodies to the antigen attached thereto.

Also provided by this invention is an extraction device for extracting Streptococcus A antigen from a biological specimen suspected of containing Streptococcus A organisms comprising:

(i) a water-insoluble container having affixed internally a dried, binder-free coating of an extraction reagent which is necessary for nitrous acid extraction of the antigen from a Streptococcus A organism, and (ii) an applicator means for collecting and depositing the biological specimen within the container.

A method for the determination of Streptococcus A antigen comprises:

A. contacting a biological specimen suspected of containing Streptococcus A organisms with first and second extraction reagents necessary for nitrous acid extraction of antigen from the organisms, the first reagent provided in a dried, binder-free coating on a water-insoluble substrate, and the second reagent provided in an aqueous solution, B. neutralizing the resulting solution of extracted antigen, C. reacting the extracted antigen with antibodies to the antigen so as to form a reaction product of antigen and antibodies, D. separating the reaction product from unreacted materials, and E. determining the amount of either the reaction product or the unreacted materials.

A preferred method for the determination of Streptococcus A antigen in a biological specimen comprises:

A. contacting a biological specimen suspected of containing Streptococcus A organisms with a water-insoluble substrate having thereon a dried, binder-free coating of a first extraction reagent which is necessary for nitrous acid extraction of antigen from the organisms, B. substantially simultaneously with contacting step A, contacting the specimen with an aqueous solution of a second extraction reagent which is necessary for the nitrous acid extraction, C. incubating the resulting extraction solution for up to 5 minutes at a temperature of up to about 90° C., D. neutralizing the extraction solution, E. in a test device, contacting the neutralized extraction solution with an immunoreactive reagent for the antigen comprising water-insoluble particles having antibodies to the antigen attached thereto to form a agglutinated reaction product of the antibodies and the antigen, F. separating the agglutinated reaction product from unreacted materials, and G. determining the amount of either the agglutinated reaction product or the unreacted materials.

The present invention provides a number of advantages over known assays for Streptococcus A antigen. It avoids the use of acetic acid or other objectionable reagents. Moreover, while it utilizes a on volatile acid, it further avoids the use of a binder material to immobilize the reagent on a substrate of some type. As noted above, the use of a binder material is disadvantageous because of the additional material and manufacturing costs and operations required. A binder material may be suitable for a laboratory assay, but high volume commercial manufacturing operations must be less costly in a highly competitive market.

Further, the present invention utilizes a neutralization step in the assay in order to reduce or eliminate the adverse effects of highly acidic conditions on antibody molecules and agglutination reagents which have free carboxyl groups. The highly acidic environment of the antigen extraction procedure severely effects free carboxyl groups on antibody molecules as well as those on polymeric particles. Hence, the problems noted with the assay described in U.S. Pat. No. 4,673,639 (noted above) are avoided.

DETAILED DESCRIPTION OF THE INVENTION

The present invention provides a diagnostic test for Streptococcus A which can be performed in a very short time, that is usually less than about 10 minutes, and without the use of complicated equipment. This permits the test to be performed in a doctor's office and enables the doctor to determine a course of treatment based upon the results of the test the same day. The test detects the presence of Streptococcus A antigen in a biological sample, such as a swab specimen from the throat, urine specimen or sample of another aqueous liquid. Such biological samples can be tested with or without pretreatment (for example, filtration) to remove unwanted debris or interferents.

The test kit of the present invention includes a water-insoluble substrate having thereon a dried, binder-free coating of a first extraction reagent (described below). The substrate can be of any suitable configuration, construction or material as long as it is water-insoluble and inert to the reactions which are used to assay for antigen. In the simplest form, the substrate can be a test tube, glass slide, microtube, test slide, filter paper strip or any other suitable material to which the extraction composition can be affixed to one or more surfaces or cavities and dried without the use of a binder material. The substrate composition can be any suitable neutral or synthetic material (for example, glass, polymeric materials, cellulosic materials and others known in the art).

In a preferred embodiment, the substrate is a container which is part of an extraction device, the container being designed so that the antigen can be extracted from a biological specimen within the container using the needed reagents. Such an extraction device can also include an applicator means for collecting and depositing the biological specimen within the container. An applicator means usually includes an applicator stick and a fibrous swab at one end thereof. Useful applicator means for Streptococcus A tests are known in the art, for example, in U.S. Pat. No. 4,618,576 (noted above). In its simplest form, the extraction device can be a simple cup with a holder for holding an applicator means. A first extraction reagent is deposited on the inside of the cup.

It is known that nitrous acid is a useful chemical for extracting Streptococcus A antigen from the organisms, but it is also known to be unstable. Hence, it is preferable to use a first and second reagent which react with each other to provide nitrous acid immediately during the extraction procedure. Usually, these reagents include a nitrite and an acid which reacts with the nitrite to provide nitrous acid.

One of these reagents is present in dried form on the substrate or extraction device described above. It is not important which one it is, although it is preferably the nonvolatile acid (described below). The first reagent is not mixed with any binder materials as taught in U.S. Pat. No. 4,673,639 (noted above). The dried reagent is nonvolatile and compositionally stable at ambient conditions (that is, about 18°-30+C.). It is optional for the first reagent to be mixed with one or more inert addenda in dried form (for example, surfactants, buffers or other materials known to one skilled in the art).

The extraction reagent is applied to the substrate in a suitable way and drying it under suitable conditions.

The first reagent is preferably a nonvolatile organic acid which has a melting point equal to or greater than about 18° C., and a pKa of about 5 or less. Examples of useful organic acids include, but are not limited to citric acid, malonic acid, phenylacetic acid, oxalic acid, glycolic acid, chloroacetic acid, trichloroacetic acid, fluoroacetic acid, bromoacetic acid, idoacetic acid, succinic acid, glutaric acid, adipic acid, pimelic acid, suberic acid, benzoic acid, benzene sulfonic acid, p-toluene sulfonic acid, azelaic acid and sebacic acid. The carboxylic acids noted above are particularly useful, with citric acid most preferred.

A second extraction reagent needed for the extraction procedure is a nitrite. Useful nitrites include, but are not limited to, inorganic nitrites such as sodium, potassium, lithium, calcium, strontium, barium and silver nitrites, and organic nitrites such as butyl and isoamyl nitrites. Sodium and potassium nitrites are preferred, and sodium nitrite is most preferred. While one extraction reagent (for example, the organic acid) is usually supplied in the kit in dried form on the substrate described above, the other reagent (for example the nitrite) is generally supplied in an aqueous solution. This solution can optionally contain surfactants or other addenda inert to the reaction to produce nitrous acid.

The concentration of nitrite and organic acid combined in the resulting extraction solution can be varied widely depending upon the particular compounds used, their water solubility and the suspected amount of antigen present in the test sample. More particularly, the amount of nitrite present is at least about 0.05 molar, and can be from about 2 to about 12 molar. The organic acid is generally present in an amount of at least about 0.01 molar, and preferably in amount of from about 0.01 to about 1 molar.

The test kit also contains a neutralizing solution having a pH of from about 5 to about 10, and preferably from about 6.5 to about 8.5. This solution is used to neutralize the extraction solution after extraction has occurred and prior to contact with agglutination reagents. More details of the assay procedure are given below. Generally, the neutralizing solution is a suitable buffer having the desired pH. Many such buffers are known in the art. One preferred buffer is 3—(N-morpholino)propanesulfonic acid. The neutralizing solution can optionally include metal chelating agents, such as ethylenediaminetetraacetic acid.

The immunoreactive reagent supplied and used in the practice of the present invention includes either Streptococcus A antigen or antibodies to the antigen bound to the surface of suitable waterinsoluble particles (defined below). Either the particles, antigen or antibodies can be labeled in a suitable manner with a tracer material (defined below) to render the reagent detectable. The reagent can be supplied as a dried sample, or as an aqueous dispersion.

In one embodiment, the immunoreactive reagent comprises antibodies bound to the surface of waterinsoluble particles. A competitive binding assay for extracted Streptococcus A antigen in a biological specimen is carried out in this invention using the immunoreactive reagent in combination with a predetermined amount of labeled Streptococcus A antigen. Reaction products of the insoluble immunoreactive reagent with labeled and unlabeled antigen are then formed and separated from unreacted materials in a suitable manner. Either the insolubilized or soluble labeled antigen can be measured to determine the amount of antigen in the specimen.

Alternatively, antibodies can be competitively reacted with extracted antigen and an immunoreactive reagent having antigen bound to particles which are labeled in some manner.

In another embodiment, extracted antigen is allowed to bind to a suitable solid carrier material. The immunoreactive reagent is the corresponding antibody to the antigen. This antibody can be suitably labeled and the reaction product or unreacted antibody can be measured.

In still another embodiment, the Streptococcus A antigen can be determined using an immunoreactive reagent comprising antibodies attached to carrier particles in an assay wherein a labeled antibody to the antibody of the immunoreactive reagent is added. Such antibodies can be labeled with any suitable tracer, such as a radioisotope, chemiluminescent compound, colorimetric or fluorometric compound and others known in the art. For example, the antigen can be determined in a "sandwich" enzyme-label immunosorbent assay, sometimes known in the art as a "sandwich" ELISA. This technique involves the use of a first antibody (monoclonal or polyclonal) attached to the particles, and a second antibody ((monoclonal or polyclonal) which is labeled with a suitable enzyme. Both antibodies are specific to the Streptococcus A antigen. The immunoreactive reagent can be reacted with the extracted antigen prior to, simultaneously with or subsequent to reaction of the antigen with the enzyme-labeled antibody.

In a preferred embodiment, the presence of Streptococcus A antigen is detected by an agglutination method using a reagent comprising waterinsoluble particles having antibodies to Streptococcus A antigen bound in a suitable manner to the surface of the particles. Reaction (or binding) between antigen and antibody molecules then results in a linking together of the particles so that they form large agglutinates.

Suitable water-insoluble particles useful in the reagent can be natural or synthetic particles which are water-insoluble and capable of having a suitable number of antibody molecules bound thereto in some manner. Examples of useful particles include ferritin crystals, agarose particles, glass beads, polymeric particles, such as latex particles, and others known in the art. The following references describe representative useful particles: U.S. Pat. Nos. 3,700,609 (issued Oct. 24, 1972 to Tregear et al.), 3,853,987 (issued Dec. 10, 1974 to Dryer), 4,108,972 (issued Aug. 22, 1978 to Dryer), 4,258,001 (issued Mar. 24, 1981 to Pierce et al.), 4,401,765 (issued Aug. 30, 1983 to Craig et al.), 4,419,453 (issued Dec. 6, 1983 to Dorman et al.), 4,459,361 (issued July 10, 1984 to Gefter), 4,478,946 (issued Oct. 23, 1984 to Van der Merwe) and 4,591,571 (issued May 27, 1986 to Kuboyama et al). The particles useful in this invention are generally quite small, that is less than about 2 micrometers in diameter. Preferably, they have an average diameter of from about 0.1 to about 1 micrometer.

Particularly useful particles are polymeric latex particles, and more preferably they are what are known in the art as core-shell polymeric latex particles. A wide variety of monomers can be used in the preparation of such particles as long as the particles are water-insoluble. A worker skilled in the polymer chemistry art would be able to design and prepare suitable latex particles. Preferred core-shell polymeric latex particles in the practice of this invention are described in the example below. These particles have a core composed of homo- or copolymers of styrene, and a shell composed of homo- or copolymers of chloromethylstyrene or m & p-(2—chloroethylsulfonylmethyl)styrene. The present invention is particularly advantageous with polymeric particles which have free carboxyl groups on the outer surface. Such groups are sometimes useful for dispersing the particles in aqueous media and keeping them in suspension. The groups may be present in homo- and copolymers prepared from ethylenically unsaturated polymerizable monomers having carboxyl groups, including but not limited to, acrylic acid, methacrylic acid, itaconic acid and others known in the art.

While the assay of this invention can be carried out, for example, by observing the presence or absence of agglutinate using light scattering or other suitable techniques, it is preferred that the particles have sufficient tracer molecules associated therewith in order to allow quantitative determination of the species from the amount of tracer seen in either the agglutinate or in the unagglutinated residual materials. The tracer molecules can be suitably attached to the outer surface of the particles, or preferably, distributed within the particles (such as a dye). Any tracer material which allows detection of the agglutinate can be used. If ferritin crystals are used as the particles, the tracer molecules are molecules of iron inherently in those crystals. Other natural or synthetic particles can have, as tracers: radioisotopes, colorimetric compounds, fluorometric compounds, chemiluminescent compounds, phosphorescent compounds and other detectable materials known in the art. Preferably, the tracer is a radioisotope, colorimetric compound or fluorometric compound (for example, dye or rare earth chelate). A worker skilled in the art would be able to combine an appropriate tracer with the particular particle used.

In one embodiment, the tracer can be a fluorescent rare earth chelate such as a europium chelate, as described for example, in U.S. Pat. No. 4,259,313 (issued Mar. 31, 1981 to Frank et al.). In another and preferred embodiment, the tracer is a colorimetric compound which is readily detected in the agglutinate. Useful dyes are known in the art. Some dyes can be incorporated into the particles when the particles are prepared. Alternatively, the dyes are imbibed into preformed particles in such a manner that they do not leach out.

The tracer can be distributed within the particles in any suitable manner. For example, the tracer can be uniformly distributed therein as shown for example in U.S. Pat. No. 3,853,987 (noted above). Preferably, the tracer molecules are located in a restricted area of the particles, for example, near the surface or predominantly in the interior thereof. In the preferred core-shell particles, the tracer can be in either the core or shell, but most preferably, substantially all of the tracer is in the core of the particles.

Streptococcus A antigen or antibodies thereto are bound to the outer surfaces of the particles in a suitable manner, for example by adsorption or covalent attachment. Attachment can be achieved using known techniques, as described for example in the references cited above. Covalent attachment is preferred as the molecules are less likely to be removed from the particles. When covalently attached, the antigen or antibody molecules can be bound directly to the particles or through suitable linking groups. Either monoclonal or polyclonal antibodies can be used. Antibodies can be obtained commercially or prepared using known techniques. Polyclonals, for example, are generally prepared by injecting antigen into suitable mammals which then generate the antibodies which can be removed for use. Monoclonals are obtained using standard hybridoma technology.

The test kit of this invention can optionally comprise a wash solution suitable for washing unreacted materials from reacted materials. A preferred wash solution has a pH of from about 5 to about 10 and which contains an ionic compound providing an ionic strength of at least about 0.25 as described in copending and commonly assigned U.S. Ser. No. 19,850, filed Feb. 27, 1987 by Snyder et al.

While the present invention is not so limited, the assay for Streptococcus A antigen can be carried out using a suitable test device which comprises a microporous membrane for separating reacted materials from unreacted materials, as in an agglutination assay. Such a device can have one or more wells into which extracted antigen is deposited for reaction with the immunoreactive reagent. This reagent can be added to the device separately during the assay or with the extracted antigen, or incorporated therein at the time of manufacture. An example of such a test device is described and claimed in copending and commonly assigned U.S. Ser. No. 19,810 filed on Feb. 27, 1987 by Hinckley. Other variations of useful test devices would be within the purview of an ordinary worker skilled in the art.

In general, extraction of antigen is accomplished by contacting the biological specimen, for example, on a swab, with the extraction reagents in solution (for example, in the extraction device) in a manner such that the reagents accomplish the desired result. Often, an incubation period (up to about 5 minutes) at a temperature up to about 90° C. is required. Longer periods at lower temperatures can also be used. Preferably, the incubation is for up to 1 minute at up to 90° C., or up to 5 minutes at up to 30° C. Most preferably, the incubation is carried out for about 1 minute at about 25° C. (room temperature). The advantage of the preferred embodiment of the present invention is that extraction can occur quickly making the overall assay very rapid.

After neutralization of the resulting extraction solution with the neutralizing solution described above, the extracted antigen is contacted with the immunoreactive reagent in a test device as described above so as to form a reaction product of antigen and antibodies.

In the preferred embodiment described above, the product is an agglutinate. Simultaneously or subsequent to contact or extracted antigen with antibody molecules to form the agglutinate, the agglutinate is also preferably contacted with a microporous water-insoluble membrane. In one embodiment, the agglutinate can be formed in a separate container and then brought into contact with the membrane. Alternatively and preferably, the agglutinate is formed in the presence of the membrane. This membrane (described in detail below) can be simply a filter means held by hand through which unagglutinated materials are filtered. Preferably, however, it is mounted in a test device in which the assay is carried out. Such a test device is described above.

Any microporous water-insoluble membrane can be used as long as it is inert to the materials used in the assay, and has the desired porosity which will allow fluids and nonagglutinated materials to pass through but which will retain agglutinated materials. In other words, the membrane pores must be large enough to allow passage of the unagglutinated particles, but not large enough to allow agglutinated particles to pass through. More particularly, the average pore size of the membrane must be at lest five times the average diameter of the water-insoluble particles described above. Preferably, the average pore size is from about 6 to about 15 times the average particle diameter. Useful membranes include polymeric materials which are commercially available from various sources, such as Pall Corp (Glen Cove, N.Y.). One useful membrane is a nylon-66 microporous membrane manufactured and marketed by that company as BIODYNE or ULTIPOR.

A suitable incubation period can be used to optimize agglutination, if desired, before or during contact with the membrane. After that period, unagglutinated residual materials are washed through the membrane while leaving the agglutinate thereon. This separation step is usually carried out within about 1 to about 10 minutes of adding the neutralized solution to the test device.

Once the unagglutinated residual materials have been washed through the membrane, the amount of antigen in either the agglutinate or residual materials can generally be determined with the unaided eye if the tracer is a readily viewable colorimetric dye. Otherwise, standard colorimetric detection equipment can be used. Other types of tracers, for example, radioisotopes, fluorescent dyes, phosphorescent dyes, and the like, require suitable detection equipment.

In the examples which follow, illustrating the practice of this invention, the materials used were obtained as follows:

casein from Sigma Chemical Co. (St. Louis, Mo.), nylon 66 membranes from Pall Corp. (Glen Cove, N.Y.), Oil Red EGN dye from Aldrich Chemical Co. (Milwaukee, Wis.), succinylated casein was prepared by reacting casein with an equal weight of succinic anhydride for four hours at 25° C., and then purifying the product by dialysis, monoclonal antibodies to Streptococcus A antigen were obtained from Streptococcus A vaccine according to the procedure described by McCarty et al., J. Exp. Med. 102, 11, 1955, and the remainder either from Eastman Kodak Company (Rochester, N.Y., U.S.A.) or Cetus Corporation (Emeryville, Calif.) or prepared using standard procedures and readily available starting materials.

EXAMPLE 1

Agglutination Determination of Streptococcus A using Citric Acid in Extraction Procedure This example demonstrates the practice of the present invention for the determination of Streptococcus A antigen.

Core-shell polymeric latex particles were prepared using core-shell polymerization techniques. A red dye (Oil Red EGN) was imbibed into the core of the particles using the procedures described in Belgian Patent Publication No. 843,647 (published Dec. 30, 1976). The core of the particles was composed of poly(styrene-co-2—acetoacetoxyethyl methacrylate) (70:30 weight ratio) while the shell was composed of poly(M,p—chloromethylstyrene). The average diameter of the particles was about 0.45 micrometer. Monoclonal antibodies to Streptococcus A antigen and casein were immobilized on these particles as follows: to 0.6 ml of 50 mmolar borate buffer (pH 8.5) was added 0.1 mg of total protein comprised of a 10:1 mixture of anti-Strep A antibody (2.9 mg/ml solution in phosphate buffered saline solution, known in the art as PBS) and casein (10 mg/ml water). After mixing, 41.5 μl of a 5% suspension of the polymeric latex particles were added (to provide 0.3% solids) and the resulting solution was rotated (end-over-end) for 24 hours at 37° C. to effect covalent attachment of the antibody to the outer surfaces of the particles and the formation of the agglutination indicator reagent.

A solution of succinic anhydride (10 mg/ml dimetyl sulfoxide) was added to a suspension of the agglutination indicator reagent described above at a weight ratio of 1 part anhydride to 1 part total protein. The resulting suspension was mixed for four hours at 25° C., centrifuged for 5 minutes at 7000 rpm and the resulting pellet was resuspended in 0.1 molar glycine buffer (pH 8.5) to a concentration of 0.3% solids.

An isolate of Streptococcus A obtained from a local hospital was used in the assays of this example. Streptococcus A antigen was extracted from an isolate at 25° C. for 1 minute using a solution of equal volumes of sodium nitrite (8 molar) and citric acid (0.2 molar). The extraction solution was then neutralized with an equal volume of 3—(N-morpholino)-propanesulfonic acid buffer (2 molar, pH 7.5) containing ethylenediaminetetraacetic acid (75 mmolar).

A nylon 66 microporous membrane (5 μm average pore size) was incorporated into a test well of a disposable test device like that described and claimed in U.S. Ser. No. 19,810 of Hinckley, noted above, and pretreated by washing with 100 μl of a 2% succinylated casein solution.

A mixture of sodium chloride (80 μl, 1 molar), the agglutination indicator reagent suspension described above (40 μl), and extracted antigen (80 μl) containing about $4.2\times10^5$ colony-forming units was added to the test well of the test device containing the membrane, and incubated therein for two minutes at 25° C. The fluid was then allowed to drain into a compartment below the membrane, and the agglutinate on the membrane was washed with 150 μl of a wash fluid having an ionic strength of about 1.0.

After the washing step, the amount of dye in the agglutinate on the membrane was measured at 540 nm using reflectance measuring equipment. The Williams-Clapper transform (J. Optical Soc. Am. 43, p. 595, 1953) was used to calculate transmission density values. The agglutinate on the membrane was readily observable and had a significantly greater density value than the density of a background control (the difference was 0.148). These data indicate that the present invention is useful for the extraction and determination of Streptococcus A antigen in a biological sample.

EXAMPLE 2

Determination of Streptococcus A Using Succinic Acid for Antigen Extraction

The procedure and reagents described in Example 1 were used in this example except that citric acid was replaced with succinic acid.

Streptococcus A antigen was extracted from the microbial isolate for one minute at 25° C. using a solution of 90 μl citric acid (0.2 molar) and 90 μl of sodium nitrite (8 molar). The extraction solution was then neutralized with tricine buffer (1 molar, pH 8.6) and ethylenediaminetetraacetic acid (25 mmolar).

A mixture of the agglutination reagent (90 μl) and the extraction solution (40 μl) was mixed for two minutes at 25° C. It was then added to a disposable test device containing a microporous membrane (BIODYNE A filter from Pall Corp.) which had been pretreated with succinylated casein (1.07 mg/cm$^2$), and incubated thereon for two minutes at 25° C. The fluid was then allowed to drain through the membrane, and the agglutinate on the membrane was washed with 150 μl of a wash fluid having an ionic strength of about 1.0.

The amount of dye in the agglutinate was then measured as described in Example 1 and similar results were obtained as with citric acid. This indicates that succinic acid can be effectively used in extracting the Streptococcus A antigen in the practice of this invention.

EXAMPLE 3

Comparative Test

This example shows the effect of omitting a neutralization step in this invention.

Streptococcus A antigen was extracted from a microbial isolate for about 1 minute at 25° C. using a solution of citric acid (10 μl, 1.2 molar) and sodium nitrite (120 μl, 8 molar) to form a first test solution. A second extraction solution was similarly prepared except that distilled water was used in place of the microbial isolate (that is, it had no antigen). Neither extraction solution was neutralized.

A solution of sodium chloride (80 μl, 1 molar), agglutination reagent as described in Example 1 (40 μl) and the first extraction solution described above (40 μl) were successively added to the test wells of a test device like that described in Example 1, and incubated therein for about 2 minutes at 25° C.

Likewise, the sodium chloride solution, agglutination reagent and second extraction solution were successively added to the test wells of a second test device and incubated.

After incubation, the fluids were allowed to drain through the membranes in the test devices, and the agglutination reagent remaining on the membranes was washed with sodium chloride solution (80 μl, 1 molar), then visually examined. An intense red color was observed in all wells of both test device. This indicates that non-specific agglutination occurred with the agglutination reagent as a result of not neutralizing the extraction solutions, so that agglutination occurred with or without the presence of antigen.

The tests described above were repeated except that the extraction solutions were mixed with the agglutination reagent in separate test tubes without neutralization. The presence of agglutination was observed in both test tubes.

The invention has been described in detail with particular reference to preferred embodiments thereof, but it will be understood that variations and modifications can be effected within the spirit and scope of the invention.

We claim:

1. A test kit for the determination of Streptococcus A antigen comprising:

(a) a water-insoluble substrate having thereon a dried, binder-free coating of a first extraction reagent which is necessary for nitrous acid extraction of said antigen from a Streptococcus A organism, *said first extraction reagent being either a nitrite or a nonvolatile organic acid which has a pKa equal to or less than about 5 and a melting point equal to or greater than about 18° C. at atmospheric pressure,*

*the nonvolatile organic acid being selected from the group consisting of citric acid, malonic acid, phenylacetic acid, oxalic acid, glycolic acid, chloroacetic acid,*

*trichloroacetic acid, fluoroacetic acid, bromoacetic acid, iodoacetic acid, succinic acid, glutaric acid, adipic acid, pimelic acid, suberic acid, benzoic acid, benzene sulfonic acid, p-toluene sulfonic acid, azelaic acid and sebacic acid,*

(b) an aqueous solution of a second extraction reagent which *is reactive with said first extraction reagent and which* is necessary for said nitrous acid extraction, (c) a neutralizing solution having a pH of from about 5 to about 10, and (d) a sample of an immunoreactive reagent comprising water-insoluble particles having either Streptococcus A antigen or antibodies to said antigen attached thereto.

[2. The kit of claim 1 wherein said first extraction reagent is a nonvolatile organic acid which has a pKa equal to or less than about 5 and a melting point equal to or greater than about 18° C. at atmosphere pressure.]

[3. The kit of claim 2 wherein said organic acid is selected from the group consisting of citric acid, malonic acid, phenylacetic acid, glycolic acid, chloroacetic acid, trichloracetic acid, fluoroacetic acid, bromoacetic acid, iodoacetic acid, succinic acid, glutaric acid, adipic acid, pimelic acid, suberic acid, benzoic acid, benzenesulfonic acid, p-toluene sulfonic acid, azelaic acid and sebacic acid.]

4. The kit of claim 1 wherein said *first extraction reagent is said organic acid, and said* second extraction reagnet is a nitrite.

5. The kit of claim 4 wherein said nitrite is either sodium nitrite or potassium nitrite.

6. The kit of claim 1 wherein said immunoreactive reagent comprises antibodies to said antigen, and has a tracer associated therewith.

7. The kit of claim 6 wherein said tracer is a dye within said particles.

8. The kit of claim 1 further comprising a disposable test device in which an assay for said antigen is carried out.

9. A test kit for the determination of Streptococcus A antigen comprising:

(a) a water-insoluble substrate having thereon a dried, binder-free coating of a nonvolatile organic acid which has a pKa equal to or less than about 5 and a melting point equal to or greater than about 18° C. at atmosphere pressure, said acid being selected from the group consisting of citric acid, malonic acid, phenylacetic acid, glycolic acid, chloroacetic acid, trichloroacetic acid, fluoroacetic acid, bromoacetic acid, iodoacetic acid, succinic acid, glutaric acid, adipic acid, pimelic acid, suberic acid, benzoic acid, benzenesulfonic acid, p-toluene sulfonic acid, azelaic acid and sebacic acid (b) an aqueous solution of sodium nitrite or potassium nitrite, (c) a neutralizing solution having a pH of from about 5 to about 10, (d) a sample of an immunoreactive reagent for said antigen comprising water-insoluble polymeric particles having antibodies to said antigen covalently attached thereto, and further having free carboxyl groups on the other surfaces and dye molecules therewithin, (e) a disposable test device for carrying out an assay for said antigen, said test device comprising a microporous membrane, (f) a wash solution, (g) an applicator means comprising an applicator stick having a swab at one end for collecting a test specimen.

10. A method for the determination of Streptococcus A antigen in a biological specimen comprising:

A. contacting a biological specimen suspected of containing Streptococcus A organisms with a water-insoluble substrate having thereon a dried, binder-free coating of a first extraction reagent which is necessary for nitrous acid extraction of antigen from said organisms, *said first extraction reagent being either a nitrite or a nonvolatile organic acid which has a pKa equal to or less than about 5 and a melting point equal to or greater than about 18° C. at atmospheric pressure,*

*the nonvolatile organic acid being selected from the group consisting of citric acid, malonic acid, phenylacetic acid, oxalic acid, glycolic acid, chloroacetic acid, trichloroacetic acid, fluoroacetic acid, bromoacetic acid, iodoacetic acid, succinic acid, glutaric acid, adipic acid, pimelic acid, suberic acid, benzoic acid, benzene sulfonic acid, p-toluene sulfonic acid, azelaic acid and sebacic acid,*

B. substantially simultaneously with contacting step A, contacting said specimen with an aqueous solution of a second extraction reagent *which is reactive with said first extraction reagent and* which is necessary for said nitrous acid extraction.

C. incubating the resulting extraction solution for up to 5 minutes at a temperature up to about 90° C., D. neutralizing said extraction solution, E. in a test device, contacting said neutralized extraction solution with an immunoreactive reagent for said antigen comprising water-insoluble particles having antibodies to said antigen attached thereto to form [a] *an* agglutinated reaction product of said antibodies and said antigen, F. separating said agglutinated reaction product from unreacted materials, and G. determining the amount of either said agglutinated reaction product or said unreacted materials.

11. The method of claim 10 wherein said biological specimen and said first and second extraction reagents [ar] *are* contacted within an extraction device comprising said water-insoluble substrate to which is affixed said first extraction reagent by inserting an applicator means carrying said specimen into said container containing said first and second extracting reagents.

12. The method of claim 10 wherein said incubation is carried out for about 1 minute at room temperature.

13. The method of claim 10 wherein said extraction solution is neutralized to a pH of from about 5 to about 10.

14. The method of claim 10 wherein said immunoreactive reagent comprises water-insoluble polymeric particles having antibodies to said antigen covalently attached thereto, and further having free carboxyl groups on the outer surfaces and dye molecules therewithin.

15. The method of claim 10 wherein said test device contains a microporous membrane for separating said agglutinated reaction product from said unreacted materials.

16. A method for the determination of Streptococcus A antigen comprising:

A. contacting a biological specimen suspected of containing Streptococcus A organisms with first and second extraction reagents necessary for nitrous acid extraction of antigen from said organisms, said first reagent provided in a dried, binder-free coating on a water-insoluble substrate, *said first extraction reagent being either a nitrite or a nonvolatile organic acid which has a pKa equal to or less than about 5 and a melting point equal to or greater than about 18° C. at atmospheric pressure, and said second reagent being reactive with said first extraction reagent and* provided in an aqueous solution,

*the nonvolatile organic acid being selected from the group consisting of citric acid, malonic acid, phenylacetic acid, oxalic acid, glycolic acid, chloroacetic acid, trichloroacetic acid, fluoroacetic acid, bromoacetic acid, iodoacetic acid, succinic acid, glutaric acid, adapic acid, pimelic acid, suberic acid, benzoic acid, benzene sulfonic acid, p-toluene sulfonic acid, azelaic acid and sebacic acid,*

B. neutralizing the resulting solution of extracted antigen,

C. reacting said extracted antigen with antibodies to said antigen so as to form a reaction product of antigen and antibodies, D. separating said reaction product from unreacted materials, and E. determining the amount of either said reaction product or the unreacted materials.

* * * * *